United States Patent
Pavlidis

(10) Patent No.: US 8,401,261 B2
(45) Date of Patent: Mar. 19, 2013

(54) IMAGING FACIAL SIGNS OF NEURO-PHYSIOLOGICAL RESPONSES

(75) Inventor: Ioannis Pavlidis, Houston, TX (US)

(73) Assignee: University of Houston System, Houston, TX (US)

(*) Notice: Subject to any disclaimer, the term of this patent is extended or adjusted under 35 U.S.C. 154(b) by 1063 days.

(21) Appl. No.: 12/237,889

(22) Filed: Sep. 25, 2008

(65) Prior Publication Data

US 2009/0080730 A1 Mar. 26, 2009

Related U.S. Application Data

(60) Provisional application No. 60/975,073, filed on Sep. 25, 2007.

(51) Int. Cl.
*G06K 9/00* (2006.01)

(52) U.S. Cl. ........................................... 382/128

(58) Field of Classification Search .................. 382/115, 382/117, 118, 128–134
See application file for complete search history.

(56) References Cited

U.S. PATENT DOCUMENTS

| | | | | |
|---|---|---|---|---|
| 5,309,921 A * | 5/1994 | Kisner et al. | ................. | 600/532 |
| 5,800,360 A * | 9/1998 | Kisner et al. | ................. | 600/532 |
| 6,996,256 B2 * | 2/2006 | Pavlidis | ................. | 382/118 |
| 7,942,824 B1 * | 5/2011 | Kayyali et al. | ................. | 600/538 |
| 2006/0258921 A1 * | 11/2006 | Addison et al. | ................. | 600/323 |
| 2008/0051648 A1 * | 2/2008 | Suri et al. | ................. | 600/407 |

* cited by examiner

*Primary Examiner* — Phat X Cao
*Assistant Examiner* — Diana C Vieira
(74) *Attorney, Agent, or Firm* — Conley Rose, P.C.

(57) ABSTRACT

The invention provides an integrated framework for detecting peripheral sympathetic responses through imaging. The measurements may be performed on three facial areas of sympathetic importance, that is, periorbital, supraorbital, and maxillary. Because the imaging measurements are thermal in nature and comprise multiple components of variable frequency (i.e., blood flow, sweat gland activation, and breathing), wavelets are used as the image analysis framework. The image analysis may be grounded on GSR signals.

10 Claims, 6 Drawing Sheets

IMAGING FACIAL SIGNS OF NEURO-PHYSIOLOGICAL RESPONSES

CROSS-REFERENCE TO RELATED APPLICATIONS

This application claims the benefit under 35 U.S.C. §119 (e) of U.S. Provisional Patent Application No. 60/975,073 filed Sep. 25, 2007, the disclosure of which is hereby incorporated herein by reference.

STATEMENT REGARDING FEDERALLY SPONSORED RESEARCH OR DEVELOPMENT

Research leading to the present invention was supported in part by the federal government under a grant from the National Science Foundation (Grant No. ISS-0741581). The United States government may have certain rights in the invention.

BACKGROUND

1. Field of the Invention

This invention relates to a method for detecting peripheral sympathetic responses via imaging.

2. Description of the Related Art

The Autonomic Nervous System (ANS) and particularly its sympathetic division has been the object of intense study in neurophysiology and psychophysiology. The sympathetic division readies the body for a crisis that may require sudden, intense physical activity. It is a primal survival mechanism. Therefore, methodologies that scrutinize sympathetic responses are well-founded and have many applications.

When sympathetic activation occurs, an individual experiences many changes. Among these are increased activities in the cardiovascular and respiratory centers of the pons and medulla oblongata, leading to elevations in blood pressure, heart rate, breathing rate, and depth of respiration. These vital sign changes are mediated through adrenergic postganglionic fibers. Determination of sympathetic activation through vital sign monitoring is not always straightforward. Vital signs are often affected by pathophysiology and the time resolution of sympathetic activation thereof is limited by the long-lasting effect of nor-epinephrine release.

As an alternative, researchers focused efforts on sympathetic manifestations effected through cholinergic postganglionic fibers. These fibers innervate sweat glands of the skin and the blood vessels to skeletal muscles and the brain. They provide a pathway to stimulating sweat gland secretion and selectively enhancing blood flow to muscles. Cholinergic mediation results in local physiological signs (versus vital signs), which are more descriptive (least affected by pathophysiology) and fast acting (fine time resolution).

In this context, Electro-Dermal Activity (EDA) has been the gold standard for peripheral monitoring of sympathetic responses. EDA is measured through the Galvanic Skin Response (GSR), which is a simple and reproducible method for quantifying sweat gland activation in the palm. The exposed part of the human body where sweat gland activation is considered to be the strongest during arousal is the palm. Therefore, the GSR sensor is attached to the palm or the fingers and the corresponding signal represents a change in the electrical properties of the skin of the palm. Alternatively, EDA may be captured through a palm thermistor, which registers the full thermoregulatory phenomenon including changes both in blood flow and sweat gland activation.

In recent years, it has been demonstrated that during arousal additional physiological signs materialize on the face. Specifically, increased blood flow in the periorbital[1,2] and supraorbital[3] areas are ubiquitous manifestations of stress. Thermal imaging methodology may be used to extract both the periorbital and supraorbital signals. This methodology has introduced a paradigm shift in peripheral neurophysiologic and psychophysiological studies in multiple ways. Information obtained for the face via thermal imaging may be compared with conventional palm information.

A need exists for improved image-based neurophysiological methodologies which may be linked with traditional probe-based methodologies. Specifically, it would be useful to have image-based neurophysiological methodologies whereby measurements performed on facial areas of sympathetic importance, including periorbital, supraorbital, and/or maxillary are used to monitor sympathetic responses. Analysis of the sympathetic importance of the maxillary area in particular may help link traditional probe-based methodologies with the herein disclosed image-based neurophysiological methodology.

SUMMARY

Herein disclosed is contact-free two-dimensional (2D) sensing of readily-accessible tissue (i.e., regions of the face) which is novel in light of the conventional contact-probe one-dimensional (1D) sensing of less accessible tissue (e.g., palm or finger).

According to the disclosed methodology, motion effects may be canceled to a degree by tissue tracking technology. This tissue tracking technology may reduce the restrictions on a subject during experimentation and monitoring.

According to the disclosed methodology, measurements are effected through computation rather than via conventional electronic transduction.

In an embodiment, the invention involves an integrated framework for detecting peripheral sympathetic responses through imaging. In embodiments, measurements are performed on three facial areas of sympathetic importance. The three facial areas may comprise the periorbital, supraorbital, and maxillary areas. Also disclosed herein is a method for quantifying sympathetic responses on the face. In embodiments of the method for detecting peripheral sympathetic responses, wavelets are used as the image analysis framework. The use of wavelets may be effective due to the fact that the imaging measurements are thermal in nature and comprise multiple components of variable frequency (i.e., blood flow, sweat gland activation, and breathing). In embodiments, the image analysis is grounded on Galvanic Skin Response (GSR) signals.

Herein disclosed is a method for quantifying at least one sympathetic response on the face, the method comprising measuring signals from at least one facial region selected from the group consisting of supraorbital, periorbital, and maxillary regions. The sympathetic responses may be quantified through measurement of at least one selected from the group consisting of blood flow in the facial/ophthalmic arteriovenous complex, blood flow in the supraorbital area, perspiration in the supraorbital area, and perspiration in the maxillary area. At least one measurement may be obtained via thermal imaging.

The method may further comprise obtaining of at least one corroborating probe signal selected from palm perspiratory signals extracted through GSR, thermal signals extracted through thermistor sensors, and breathing signals extracted through a piezo-respiratory belt transducer. At least one of the corroborating probe signals may be synchronized with the measurement via thermal imaging. The at least one sympathetic response may be quantified through wavelets analysis. The analysis may comprise a multi-resolution wavelets approach.

Also disclosed is a method for modeling Galvanic Skin Response (GSR) signal data, the method comprising segmenting the signal data into segments and approximating each segment using a mathematical function. At least one of the curve segments may be further divided into one or more subsegments. Approximation using a mathematical function may be performed separately for each curve segment, each subsegment, or both. The mathematical function may be chosen from the group consisting of Laplace distribution functions, Gaussian distribution functions, Lorentzian distribution functions, Delta distribution functions, exponential functions, and linear functions. The mathematical function may be a truncated form. In embodiments, each segment is further segmented into a Left Subsegment, a Right Subsegment, and a Left Stimulus Onset Subsegment.

Also disclosed herein is a method for localizing and/or comparing the phasic and tonic response components of at least one physiological channel selected from the group consisting of blood flow in the facial/ophthalmic arteriovenous complex, blood flow in the supraorbital area, perspiration in the supraorbital area, and perspiration in the maxillary area, the method comprising determining local maxima in the wavelet energy curves of signals obtained from the at least one physiological channel. The wavelet energy curves may be determined using a Continuous Wavelet Transform (CWT) with a Daubechies-10 mother wavelet. The method may further comprise determining if the local maxima correspond to phasic or tonic responses. The relative contributions of the phasic and tonic responses in at least one signal may be compared, in applications of the method.

Also disclosed is a method for comparing phasic and tonic response components between at least one sympathetic channel selected from supraorbital, periorbital, maxillary and the Galvanic Skin Response (GSR) by determining phasic and tonic response components for at least one sympathetic channel selected from supraorbital, periorbital, and maxillary; determining phasic and tonic response components for GSR; and comparing the phasic and tonic response components so obtained.

Also provided herein is a method of extracting a breathing component from thermal imaging signal data obtained from the maxillary area of the face by performing multi-resolution wavelets analysis on the signal data to determine phasic and tonic components, and examining the lower scale (higher frequency) wavelet energy for extraneous modulation indicative of a breathing component.

Also provided is a system for quantifying at least one sympathetic response on the face, the system comprising a thermal imager adapted to measure signals from at least one facial region selected from the group consisting of supraorbital, periorbital, and maxillary regions. The measured signal may be at least one selected from the group consisting of blood flow in the facial/ophthalmic arteriovenous complex, blood flow in the supraorbital area, perspiration in the supraorbital area, and perspiration in the maxillary area. At least one ground-truth probe may be synchronized with the thermal imager via an electronic circuit. In applications, the at least one ground-truth probe is selected from GSR sensors, thermistor sensors, piezo-respiratory belt transducers, and combinations thereof. The system may further comprise a computer in communication with the thermal imager. The computer may be adapted to perform wavelet energy analysis on the measured signal.

These and other objects, features and advantages of the present invention will become apparent with reference to the following description and drawings.

BRIEF DESCRIPTION OF THE DRAWINGS

For a detailed description of the preferred embodiments of the invention, reference will now be made to the accompanying drawings in which.

NOTATION AND NOMENCLATURE

Figure 1:
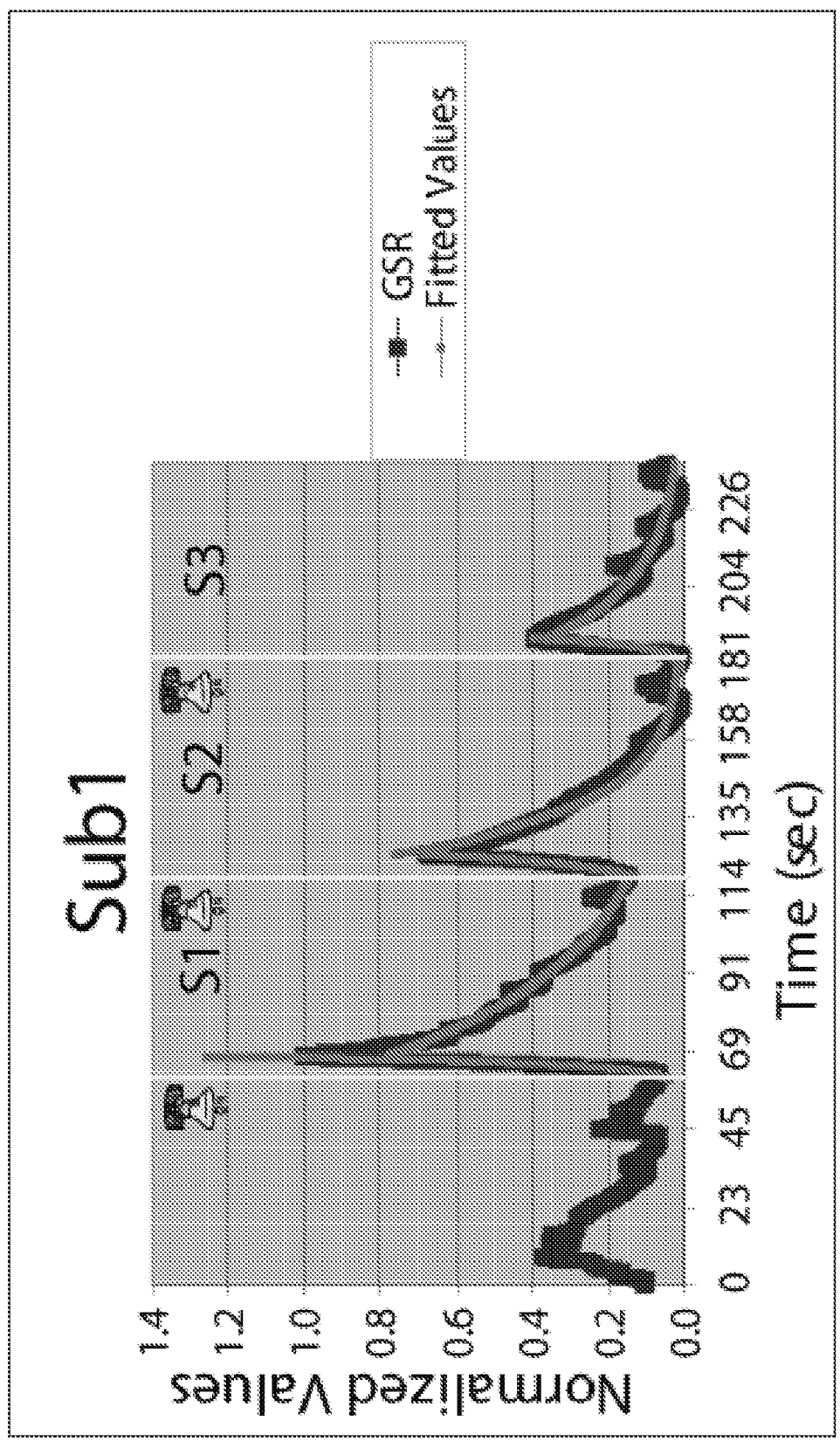
FIG. 1 is a plot of Galvanic Skin Response (GSR) segments S1, S2, and S3 along with the fitted Laplace values for subject Sub1. The stimuli occurrences are marked accordingly.

Certain terms are used throughout the following description and claim to refer to particular system components. This document does not intend to distinguish between components that differ in name but not function.

DETAILED DESCRIPTION

I. Introduction

Facial physiology may play a pivotal role in the manifestation of stress. This disclosure provides a methodological framework for sensing peripheral sympathetic responses through imaging. The disclosed imaging methodology may be used for modeling and analyzing the facial sympathetic channels.

A set of physiological signs on the face associated with stress have been identified and found to be of similar origin to the electro-dermal response on the palm. Thus, facial physiology provides redundancy to local signs in other parts of the body, such as the palm. These physiological signs manifest themselves on the footprint of the facial artery of the periorbital area (P), near the eye, as blood flow change, on the supraorbital area (S) as both blood flow change and perspiration, and the maxillary area (M) as perspiration only.

In the present invention, traditional probe-based methodologies are linked with the newer image-based neurophysiological methodologies to comparatively study facial and palm channels. The facial channels include overall thermoregulatory responses in the periorbital, supraorbital, and maxillary regions, obtained through thermal imaging. The palm channels include sweat and thermal component responses obtained through GSR and thermistor sensors respectively. The study focuses on a classic repeated arousal experiment.

A novel modeling methodology is presented to quantify the galvanic skin response or GSR signal. In this manner, the GSR signal may be used to validate the arousal experiment. It has been demonstrated with this methodology that concomitantly to the palm area, strong sweat gland activation is manifested in the maxillary area; that is, thermoregulatory information of sympathetic importance on the palm is similar to that manifested on the face. In embodiments, this newly demonstrated sympathetic thermoregulatory phenomenon manifested on the face is utilized in a method for quantifying sympathetic responses on the face. In some embodiments, perspiration in the maxillary area is sensed and computed through thermal imaging. A wavelets analysis method, described below, may be applied to all channels (periorbital, supraorbital, maxillary, GSR, and palm thermistor). The results reveal tonic (baseline) and phasic (event related) affinity of the three imaging channels (periorbital, P, supraorbital, S, and maxillary, M) to the GSR and palm thermistor channels. The integrated sensing and computation methodology disclosed herein involves the use of thermal imaging with the computation methodology based on wavelets analysis of the mean regional thermal signals. This methodology provides an alternative to existing technologies for measuring physiological responses to stimuli, enabling sensing of peripheral sympathetic responses via imaging.

The wavelet energy analysis provides a sound way to isolate the various components and reduce the noise content of the facial signals, and demonstrates quantitatively that facial sympathetic channels can be used to detect arousal.

As discussed further hereinbelow, the presence of a breathing component in the maxillary signal has been determined. As shown in Example 3 hereinbelow, from the maxillary signal, computation of breath function is feasible through multi-resolution analysis. A novel result provided herein is a method of evidencing concomitant sweat gland activation in the palm and maxillary areas. This maxillary thermoregulatory phenomenon has not heretofore been exhibited.

II. Methodology for Signal Modeling and Analysis

IIA. Modeling of GSR Signal

The GSR signal may be modeled in order to be able to draw inferences about the repeated arousal effect on a subject. This is important, as GSR may be utilized to validate the disclosed methodology for quantifying sympathetic responses on the face. Specifically, it is desirable for the modeling scheme to predict that individuals tend to habituate and therefore, GSR amplitudes tend to reduce, latencies tend to increase, and wave-shapes tend to remain unaltered. In embodiments, further discussed in Example 1 hereinbelow, the GSR signal is split into three non-overlapping segments. Segment S1 comprises the time period from 2 seconds before a first startle until 2 seconds before a second startle. Segment S2 comprises the time period from the end of S1 until 2 seconds before a third startle. Segment S3 comprises the time period from the end of S2 to the end of the experiment.

Each of the segments S1, S2, and S3 may be further divided into three subsegments. A Left Subsegment, LS, may span from the beginning of a segment to a maximum value (shortly after a startle). A Right Subsegment, RS, may span from a maximum value to the end of a segment. A Left Stimulus Onset Subsegment, LSOS, may begin at the time of a startle and last until a maximum value is reached. LSOS is thus a portion of LS and may be useful in estimating a habituation effect. In an embodiment, as discussed further hereinbelow, the method for modeling GSR signals comprises using Laplacian approximation and curve segmentation into Left Subsegment, Right Subsegment, and Left Stimulus Onset Subsegment.

The GSR signal around the stimulus is formed by the charging and discharging of an RC circuit, which closes on the palm skin during emotional sweat gland activation. Charging corresponds to arousal (LS) and is characterized by an exponential increase. Discharging corresponds to arousal waning (RS) and it follows an exponential decay. For this reason, in embodiments, the Laplace distribution is used to model the GSR signal. The probability density function is given by:

$$f(t \mid \mu, \beta) = \frac{1}{2\beta} \exp\left(-\frac{|t-\mu|}{\beta}\right), \tag{1}$$

where $\mu$ denotes the mean time parameter, while $\beta > 0$ is the scale parameter.

Although, the GSR signal is not symmetric around the local maximum value, the Laplace distribution is. Therefore, LS and RS may be modeled separately for each segment. FIG. 1 is an exemplary plot of Galvanic Skin Response (GSR) segments S1, S2, and S3 along with the fitted Laplace values for a subject Sub1, as further discussed in Examples 1 and 2 hereinbelow. For LS, a truncated Laplace distribution may be used where the $\mu$ parameter is assumed to be known (location of the maximum) and the distribution is censored to the right of the maximum. Similarly, for RS, a truncated Laplace distribution may be used where the values at the left of the maximum are censored. The scale parameters of the left and right distributions (i.e., $\beta_L$ and $\beta_R$) may then be estimated through, for example, Ordinary Least Squares (OLS) method.

For LS where $t \leq \mu$, the equation becomes:

$$\begin{aligned} y &= f(t) \\ &= \frac{1}{2\beta_L} \exp\left(-\frac{\mu-t}{\beta_L}\right) \Rightarrow \ln(y) \\ &= \left[-\frac{\mu}{\beta_L} - \ln(2\beta_L)\right] + \frac{1}{\beta_L} t, \end{aligned} \tag{2}$$

so that time t and logarithmic scale ln(y) are linearly related. OLS may be Used to estimate the slope, the inverse of which is the parameter of interest $\beta_L$.

For RS where $t \leq \mu$, the equation becomes:

$$\begin{aligned} y &= f(t) \\ &= \frac{1}{2\beta_R} \exp\left(-\frac{t-\mu}{\beta_R}\right) \Rightarrow \ln(y) \\ &= \left[\frac{\mu}{\beta_R} - \ln(2\beta_R)\right] - \frac{1}{\beta_R} t, \end{aligned} \tag{3}$$

so that time t and logarithmic scale ln(y) are linearly related, Again, OLS may be used to estimate the slope, the negative inverse of which is the parameter of interest $\beta_R$.

For LSOS linear (versus exponential) fitting map be applied, as these subsegments are nearly impulsive.

IIB. Wavelets Analysis of Sympathetic Signals

Herein disclosed is a method for quantifying sympathetic responses on the face. In embodiments, the sympathetic responses are quantified through measurement of a physiological channel selected from the group consisting of blood flow in the facial/ophthalmic arteriovenous complex, blood flow in the supraorbital area, perspiration in the supraorbital area, perspiration in the maxillary area, and combinations thereof.

The physiological channel(s) are measured using thermal imaging. In embodiments, the physiological channels are quantified through wavelets analysis as further described in Example 3 hereinbelow.

The phasic and tonic response components in any of the physiological channels may be localized through local maxima in the wavelet energy curves, as shown in Example 3 hereinbelow.

Also disclosed is a method for comparing phasic and tonic response components of at least two physiological channels selected from the group consisting of blood flow in the facial/ophthalmic arteriovenous complex, blood flow in the supraorbital area, perspiration in the supraorbital area, perspiration in the maxillary area, and combinations thereof. In embodiments, phasic and tonic response components of at least one physiological channel selected from the group consisting of blood flow in the facial/ophthalmic arteriovenous complex, blood flow in the supraorbital area, perspiration in the supraorbital area, perspiration in the maxillary area, and combinations thereof, is compared with Galvanic Skin Response (GSR).

In embodiments, thermal signals are extracted from three facial areas: periorbital, supraorbital, and maxillary. In all three cases the regions of interest may be tracked using the coalitional tracking method reported in Dowdall et al,[4] which is hereby incorporated herein in its entirety for all purposes.

Figure 2:
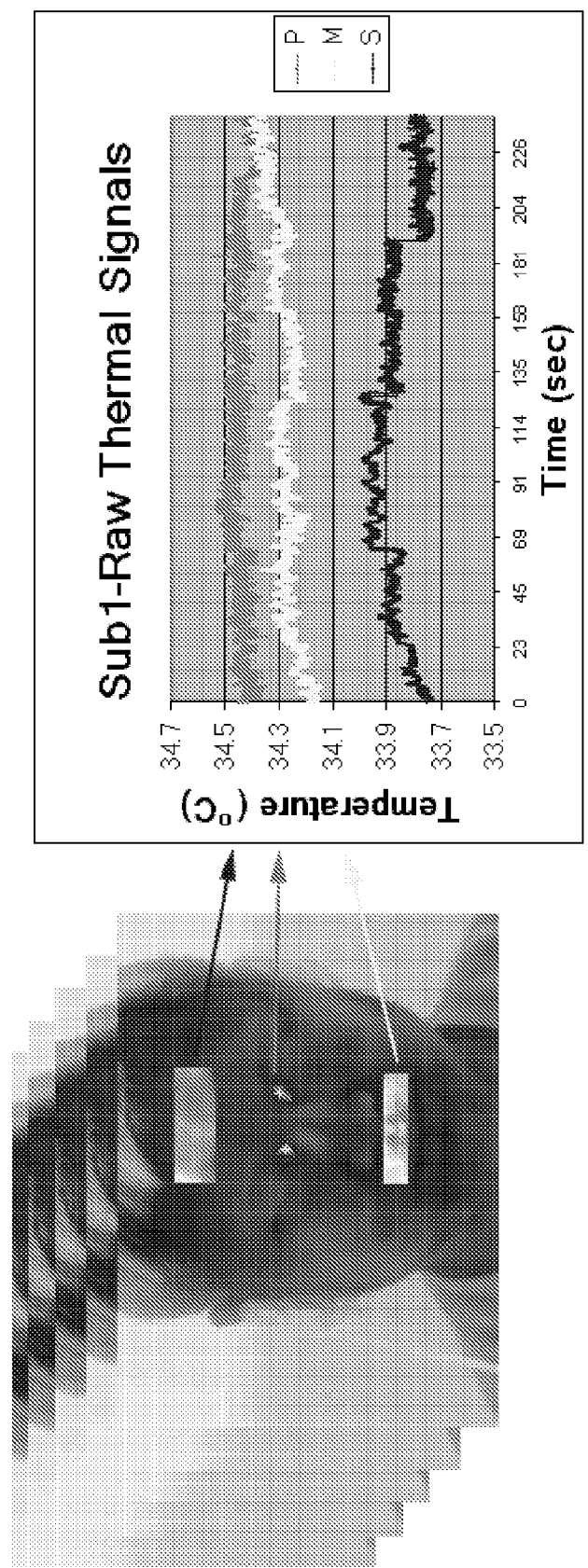
FIG. 2 is a plot of periorbital (P), supraorbital (S), and maxillary (M) regions of interest and the respective mean thermal signals along the timeline. The periorbital measurement is strictly localized on the thermal footprints of the facial artery.

In the periorbital area, the extracted signal is formed from the evolution of the mean thermal footprint of the facial arteriovenous complex. This footprint may be segmented via a fuzzy segmentation algorithm, which is seeded in the initial frame with two points in the inner orbital areas. On each subsequent frame, the seeds may be adjusted with help from the coalitional tracker. FIG. 2 is a plot of periorbital (P), supraorbital (S), and maxillary (M) regions of interest and the respective mean thermal signals along the timeline for an exemplary subject Sub1 as discussed further in Examples 1-3 hereinbelow.

The periorbital measurement is strictly localized on the thermal footprints of the facial artery. In the supraorbital area, the extracted signal is formed from the evolution of the mean thermal footprint of the entire region of interest. In the maxillary area, the extracted signal is formed from the evolution of the mean thermal footprint of the entire region of interest.

The periorbital thermal signal is a correlate of the blood supply to the orbital muscle. The supraorbital thermal signal is a correlate of the blood supply to the corrugator muscle. It may also be slightly modulated from the activation of sweat glands in the forehead. The maxillary thermal signal is a correlate of the blood perfusion in the respective area. As discussed further in Example 3 hereinbelow, the maxillary thermal signal may be significantly modulated by activation of local sweat glands. Also, the maxillary signal is periodically modulated from the thermal effect of breathing, due to the proximity of nostrils.

In embodiments, concomitantly with the three facial imaging signals, palm perspiratory and thermal signals are extracted through GSR and thermistor sensors respectively. The breathing signal may be extracted through a piezo-respiratory belt transducer. Probe signals (GSR, palm thermistor, and respiratory belt) may be synchronized with the thermal imager via an electronic circuit.

The stress content of the GSR signal has been documented in the literature.[5,6,7] To associate this content to the facial imaging signals, the disclosed methodology utilizes a multi-resolution wavelets approach. This approach is also conducive to understanding the thermal effect of breathing on the maxillary measurement and to compare the maxillary signal with ground-truth palm signals as well as with other facial signals. The typically noisy profile of facial signals (see FIG. 2) and the confounding phenomena that form them, do not allow direct modeling of the raw waveforms, as in the case of GSR (see FIG. 1). Therefore, component isolation and noise reduction may be used.

All signals having either a strong phasic or tonic component may be considered of sympathetic importance.[8] The phasic component should be at a scale that matches the inter-stimulus interval of the experiment, while the tonic component will reside at an even higher scale that spans the entire experimental time-line. Any strong extraneous modulation (e.g., breathing) in some signals should be evident in a lower scale (i.e., higher frequency), far away from the phasic and tonic scales.

Since the signals are non-stationary in nature, in order to analyze the thermal and GSR signals at different frequency scales without loss of time information, wavelet transformation over the Fast Fourier Transform (FFT) may be selected for signal analysis. To quantify the contribution of phasic, tonic, and other components in the signals, the signals may be normalized according to (4):

$$S_{norm} = [S - \text{Min}(S)] / [\text{Max}(S) - \text{Min}(S)], \quad (4)$$

where S is the signal to be normalized. Normalization is desirable in wavelet analysis because wavelet energy computed on normalized signals exposes detailed information, specifically at the lower scales.

The signals may be extended beyond the boundary limits before computing wavelet coefficients. Convolution of a wavelet with a finite length signal looks for data points beyond the signal end points. As there are no data points beyond the signal end points, this introduces an error into the wavelet energy computation, which is known as the border discontinuity error. The border discontinuity error leads to incorrect local and global maxima in wavelet energy curves. The purpose of the signal extension is to define data points beyond the signal boundary. There are many ways to extend the finite length signal. Among them, zero-padding, wrap-around and symmetric extension are popular in the image and signal analysis communities. As the present signals are non-stationary in nature, the symmetric extension technique may be desirable in this case. Selecting an appropriate signal extension length is also important in the wavelet energy computation. In embodiments, three different extension lengths, 2N, N, and N/2 may be applied, and, for each signal, the one selected which has the minimal border discontinuity error in the wavelet energy computation.

To quantify the contribution of phasic, tonic, and other components in the signals a Continuous Wavelet Transform (CWT) with a Daubechies-10 mother wavelet may be applied. The energy of each signal in all scales may then be computed. The energy curves feature global and local maxima. These maxima may be analyzed to determine if they correspond to phasic or tonic responses. The relative contributions in each signal may also be compared. For intervening phenomena having ground-truth (e.g., breathing), comparative evaluation may be performed to verify the source of the wavelet component. Example 3 hereinbelow provides an example for analyzing the maxima to determine correspondence with phasic or tonic responses.

EXAMPLES

Example 1

Data Collection

A high quality Thermal Imaging (TI) system was used for data collection. The centerpiece of the TI system was a ThermoVision SC6000 Mid-Wave Infrared (MWIR) camera[9] (NEDT=0.025C). Ten (10) thermal clips were recorded from the faces of ten (10) subjects while resting in an armchair. Concomitantly, ground-truth GSR, palm thermistor, and piezo-respiratory signals were recorded with the PowerLab 8/30, ML870 data acquisition system.[10] The data set featured subjects of both genders, different races, and with varying physical characteristics. The subjects were focused on a mental task while they were measured using the thermal imaging and contact sensors. The experiment duration was 4 minutes. Exclusion criteria were the presence of any overt peripheral neuropathy or psycho-physiological disorder. The subjects were asked to abstain from consuming vasomotor substances (e.g., caffeine and nicotine) for at least three hours prior to participating in the experiment. All participants signed the informed consent form and the study protocol was approved by the University of Houston Institutional Review Board.

The experiment was conducted in a quiet room where only two persons were present, the subject and the experiment conductor. The room lights were dimmed in order to allow the subject to relax. The subject was placed 9 feet away from the thermal camera. After all the ground-truth electrodes were attached to the subject's body, the subject was asked to relax for 10 minutes before the experiment began. This helped to reduce the effects of other stress factors that the subject may have carried in from previous events. During the experiment, the subject focused on the simple mental task of counting circles that appeared on a monitor. The subject's physiological activity was measured through thermal imaging and contact sensors. The experiment lasted 4 minutes. After the first minute, an auditory startle was delivered and after that two more were delivered, spaced one minute apart. The experiment ended about 1 minute after the delivery of the third startle. All stimuli were chosen to be natural startle sounds that people encounter in real life. Specifically, the first and third stimuli were glass breakage sounds. The second stimulus was phone ring. The second stimulus was selected to be different from the other two in an effort to raise the habituation threshold. The experiment ended one minute after the delivery of the third startle. During the data collection procedures, the experimenter was out of the subject's field of view to avoid creating distraction.

Example 2

Applying Modeling Methodology to GSR Waveforms

The GSR modeling methodology disclosed in Section IIA above was applied to each segment of every GSR waveform obtained as described in Example 1 hereinabove. Specifically, the disclosed modeling scheme was tested to verify that it shows that individuals tend to habituate and therefore, GSR amplitudes tend to reduce, latencies tend to increase, and wave-shapes tend to remain unaltered. These well-established and understood patterns of repeated arousals in normal subjects were used to validate the experimental design and execution.

Subjects were stimulated with 3 auditory startles spaced at least 1 minute apart. Therefore, 3 segments (S1, S2, S3)×3 sub-segments (LS, RS, LSOS)×10 subjects=90 cases were obtained, for which the scale parameter $\beta$ (Laplace fitting for LS and RS) or the slope (linear fitting for LSOS) had to be estimated. Table 1 presents the estimated $\beta$ parameters for the LS and RS Laplace distributions along with the linear regression slope estimates of LSOS.

TABLE 1

Estimated $\beta$ Parameters for the LS and RS Laplace Distributions along with the Linear Regression Slope Estimates of LSOS.

|  | Sub 1 | Sub 2 | Sub 3 | Sub 4 | Sub 5 | Sub 6 | Sub 7 | Sub 8 | Sub 9 | Sub 10 |
| --- | --- | --- | --- | --- | --- | --- | --- | --- | --- | --- |
| S1-LS | 2.18 | 2.68 | 1.70 | 1.94 | 7.50 | 14.54 | 4.79 | 25.39 | 4.50 | 3.87 |
| S1-LSOS | 0.20 | 0.10 | 0.15 | 0.14 | 0.13 | 0.05 | 0.06 | 0.05 | 0.08 | 0.12 |
| S1-RS | 30.40 | 33.90 | 27.11 | 40.89 | 36.88 | 82.50 | 151.47 | 38.76 | 68.08 | 25.24 |
| S2-LS | 3.75 | 3.04 | 1.77 | 8.49 | 5.69 | 26.16 | 7.89 | 13.13 | 8.29 | 9.37 |
| S2-LSOS | 0.11 | 0.07 | 0.13 | 0.08 | 0.12 | 0.03 | 0.10 | 0.04 | 0.10 | 0.11 |
| S2-RS | 13.39 | 29.46 | 34.11 | 62.67 | 22.46 | 53.43 | 44.81 | 20.71 | 61.55 | 30.69 |
| S3-LS | 1.91 | 2.51 | 2.30 | 10.13 | 2.51 | 62.46 | 15.09 | 2.28 | 10.63 | 5.49 |
| S3-LSOS | 0.09 | 0.09 | 0.12 | 0.06 | 0.12 | 0.01 | 0.03 | 0.08 | 0.07 | 0.08 |
| S3-RS | 17.93 | 11.36 | 34.25 | 66.67 | 19.12 | 31.53 | 81.62 | 108.44 | 25.21 | 13.44 |

For all stimuli (S1, S2 and S3), LS has a much smaller scale parameter than RS indicating that the phenomenon causes a steep increase and then decays at a much lower rate.

Comparing the LS parts of S1, S2, and S3, within the same subject, it was found that the 1$^{st}$ stimulus usually causes the steepest increase and subsequent stimuli result in a response that is less steep (i.e., the $\beta_L$ parameter is increasing).

Comparing the RS parts of S1, S2, and S3, within the same subject, it was found that the subject usually recovers slowly after the 1$^{st}$ stimulus (i.e., it has a high $\beta_R$ parameter). Recovery from subsequent stimuli becomes faster (smaller $\beta_R$ parameter).

Comparing the LSOS parts of S1, S2, and S3, within the same subject, it was found that the estimated (positive) slope of the linear regression decreased from S1 to S2 to S3 (habituation).

These conclusions are in accordance with the expected behavior of normal subjects, and validated the application of the methodology to GSR waveforms.

Example 3

Comparative Wavelets Analysis Results

Figure 3A:
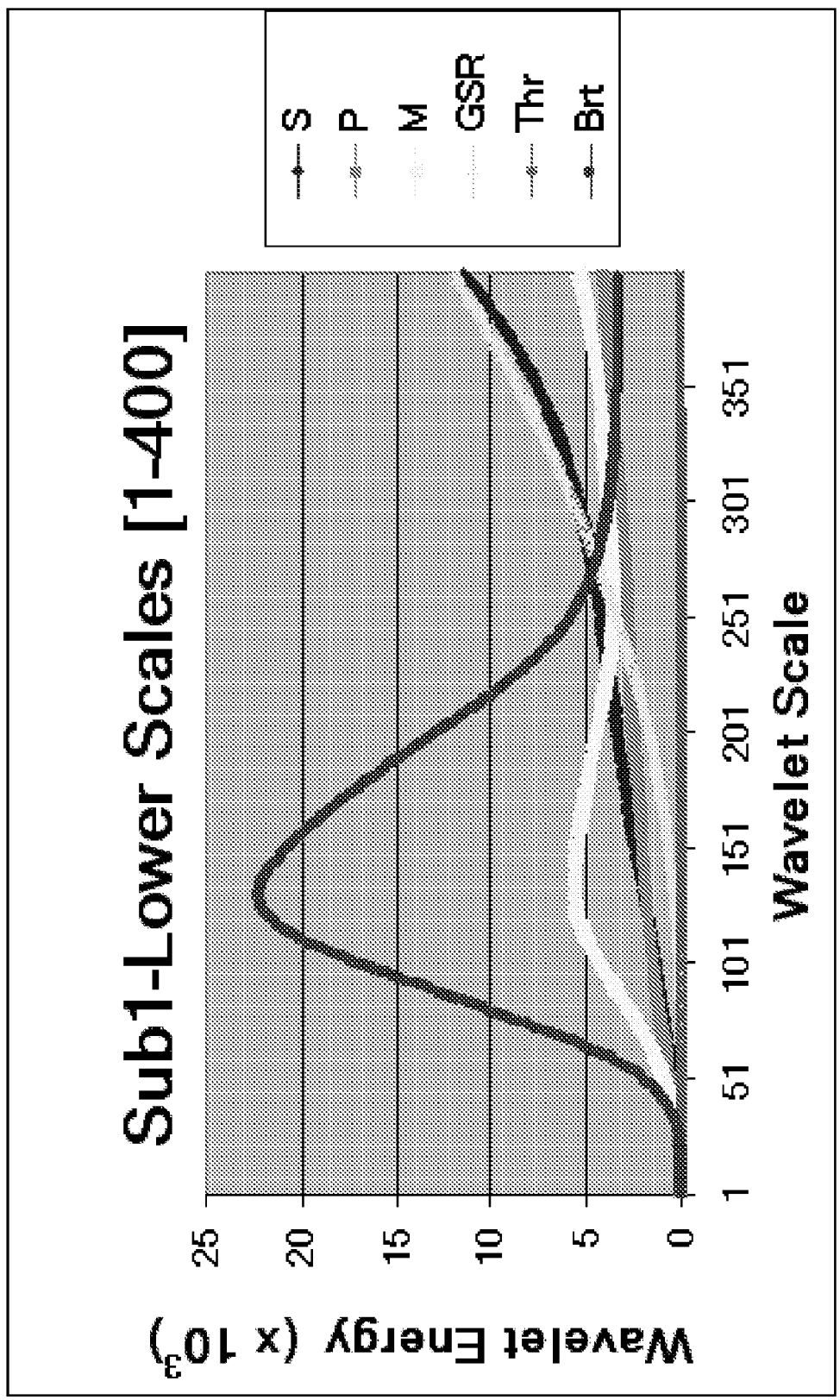
FIG. 3a is a plot of wavelet energy curves of subject Sub1 for all 6 sympathetic channels in lower scales.
Figure 3B:
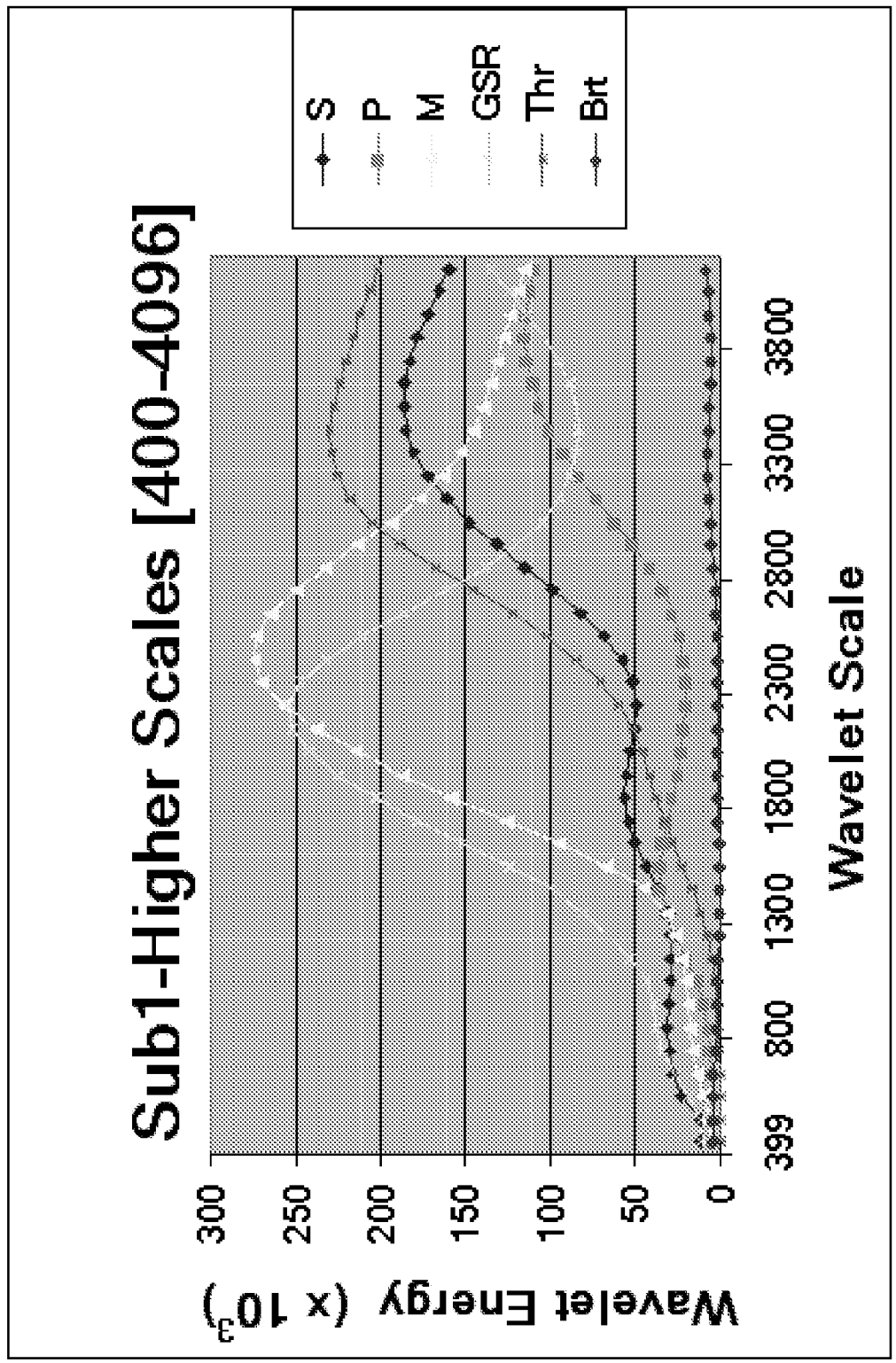
FIG. 3b is a plot of wavelet energy curves of subject Sub1 for all 6 sympathetic channels in higher scales.

The wavelets analysis methodology detailed in Section IIB hereinabove was used for all 6 sympathetic signals from all 10 subjects tested as described in Example 1. FIG. 3a shows the wavelet energy curves in lower scales of subject Sub1; FIG. 3b shows the wavelet energy curves in higher scales for subject Sub1. In lower scales (i.e., 50-250) the piezo-respiratory signal (Brt) appears to have a dominant component, as it is manifested by the high bell-shaped bulge. This is in accordance with its expected function. The second most prominent component is featured by the maxillary signal (M). This verifies the hypothesis of breathing modulation for this signal, as it is sampled in proximity to the nostrils.

In higher scales, (see FIG. 3b), for example from about 1000-3000, the GSR signal (GSR) appears to have a dominant component, as it is manifested by the high bell-shaped bulge. This is the phasic component as the scale is about ⅓ of the total scale and matches the period of the repeated stimuli in the experiment. The strong presence of a phasic component in the GSR signal is consistent with its nature. The result of an almost equally strong phasic component in the maxillary signal (M) is consistent with the hypothesis of strong sweat gland activation in the maxillary area concomitant to the palm area. Other facial signals (i.e., periorbital-P and supraorbital-S) also have a significant, but relatively weaker phasic component, which verifies sympathetic relevance thereof.

Figure 4:
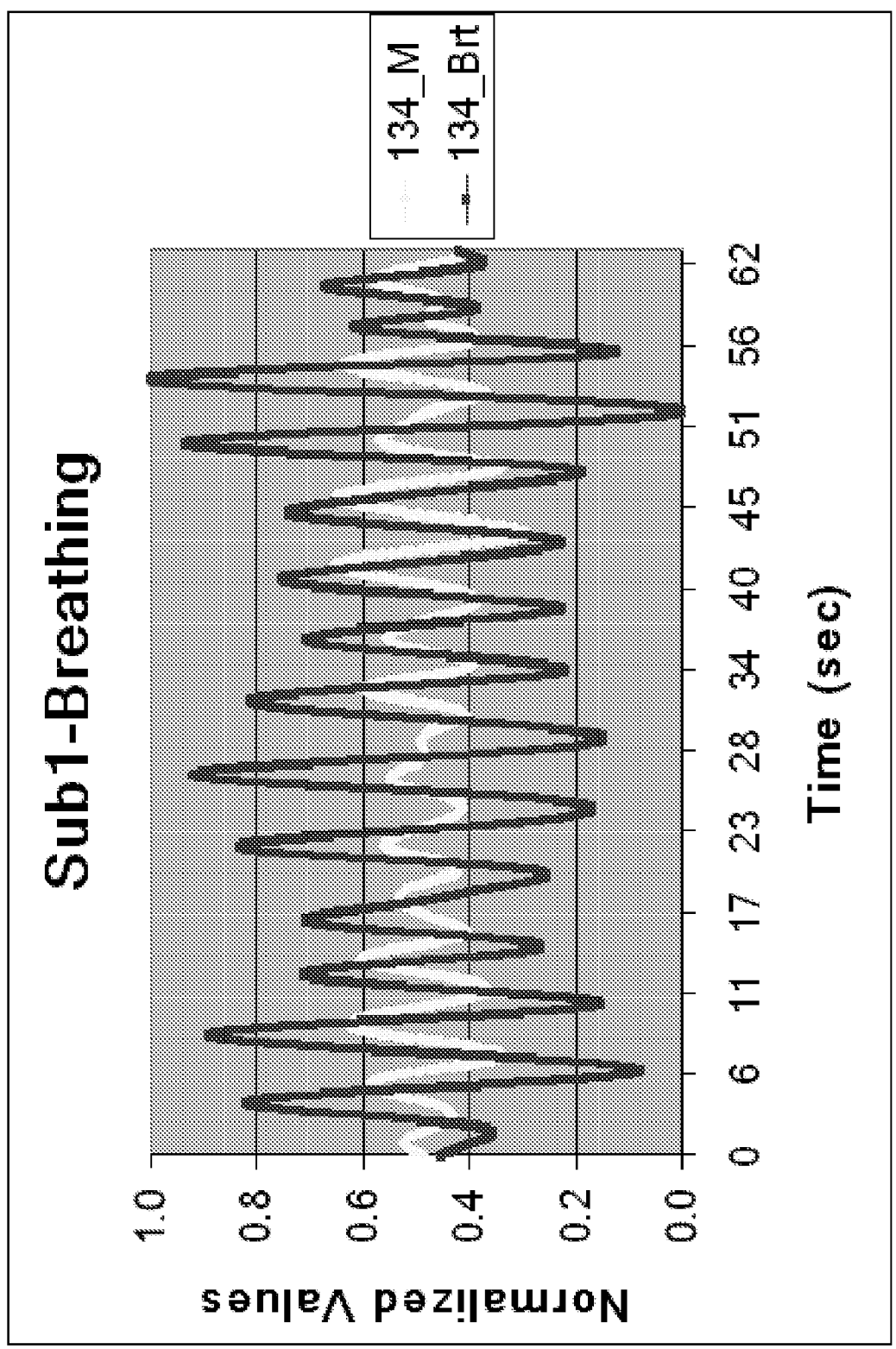
FIG. 4 is a plot of wavelet components of the breathing (Brt) and maxillary (M) signals that correspond to the respective lower scale energy maxima.

FIG. 4 is a superimposition of the wavelet components that correspond to the local energy maxima of the piezo-respiratory (Brt) and maxillary signals (M) for subject Sub1. There is a slight, but consistent phase shift due to the fact that the Brt signal is sampled around the chest while the M signal is in the vicinity of the nostrils. Other than that, the periodicity of the signals matches beat for beat. Similar results are produced for the other subjects.

The tonic components of the signals reside at the highest scales (3300-4000) and span almost the entire timeline. It is worth noting that the GSR signal has the smallest tonic component of all sympathetic channels. This is consistent with the almost unimodal nature of the GSR channel. The maxillary signal (M), which is its facial equivalent, has a much stronger tonic component. In contrast to the GSR signal, the maxillary signal contains not only local sweat gland activation information, but also thermal information related to changes in local blood perfusion. In this sense, the maxillary signal (M) is probably closer to the palm thermistor (Thr) signal.

Figure 5:
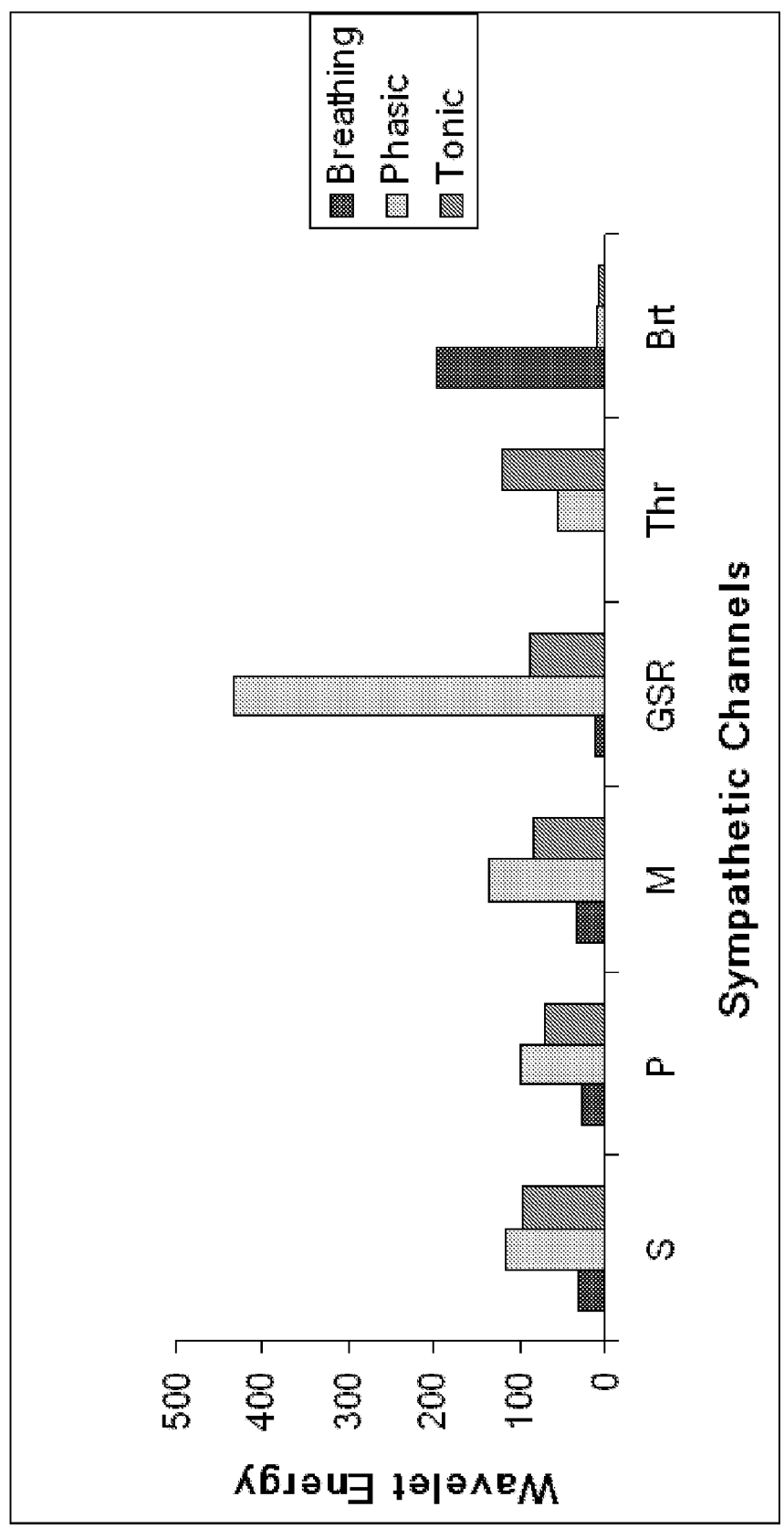
FIG. 5 is a bar graph of mean tonic, phasic, and breathing energy components for the various sympathetic channels.

In general, adrenergic and cholinergic signal components reside in non-overlapping scales, which make the adopted multi-resolution approach a desirable analysis tool. The picture emerging from the analysis of the wavelet energy curves for subject Sub1 remains relevant for the other 9 subjects in the dataset. FIG. 5 shows the mean energy of tonic, phasic, and breathing components of the various sympathetic channels for the entire data set. The conclusions extracted through the analysis of subject Sub1 still apply for the thus statistically-constructed mean subject.

While preferred embodiments of the invention have been shown and described, modifications thereof can be made by one skilled in the art without departing from the spirit and teachings of the invention. The embodiments described herein are exemplary only, and are not intended to be limiting. Many variations and modifications of the invention disclosed herein are possible and are within the scope of the invention. Where numerical ranges or limitations are expressly stated, such express ranges or limitations should be understood to include iterative ranges or limitations of like magnitude falling within the expressly stated ranges or limitations (e.g., from about 1 to about 10 includes, 2, 3, 4, etc.; greater than 0.10 includes 0.11, 0.12, 0.13, and so forth). Use of the term "optionally" with respect to any element of a claim is intended to mean that the subject element is required, or alternatively, is not required. Both alternatives are intended to be within the scope of the claim. Use of broader terms such as comprises, includes, having, etc. should be understood to provide support for narrower terms such as consisting of, consisting essentially of, comprised substantially of, and the like.

Accordingly, the scope of protection is not limited by the description set out above but is only limited by the claims which follow, that scope including all equivalents of the subject matter of the claims. Each and every claim is incorporated into the specification as an embodiment of the present invention. Thus, the claims are a further description and are an addition to the preferred embodiments of the present invention. The disclosures of all patents, patent applications, and publications cited herein are hereby incorporated by reference, to the extent they provide exemplary, procedural or other details supplementary to those set forth herein.

REFERENCES

1. Levine, J., Pavlidis, I., Cooper, M. The face of fear. The Lancet 357(9270) (2001) 1757.
2. Pavlidis, I., Eberhardt, N., Levine, J. Human behavior: Seeing through the face of deception. Nature 415(6867) (2002) 35.
3. Puri, C., Olson, L., Pavlidis, I., Starren, J. Stresscam: Non-contact measurement of users' emotional states through thermal imaging. In: Proceedings of the 2005 ACM Conference on Human Factors in Computing Systems (CHI), Portland, Oreg. (2005) 1725-8.
4. Dowdall, J., Pavlidis, I., Tsiamyrtzis, P. Coalitional tracking. Computer Vision and Image Understanding (2007).
5. Baba, M., Watahiki, Y., Matsunaga, M., Takebe, K. Sympathetic skin response in healthy man. Electromyography Clinical Neurophysiology 28 (1988) 277-283.
6. Uncini, A., Pullman, S., Lovelace, R., Gambi, D. The sympathetic skin response: Normal values, elucidation of afferent components and application limits. The Journal of Neuroscience 87 (1988) 299-306.
7. Elie, B., Guiheneuc, P. Sympathetic skin response: Normal results in different experimental conditions. Electroencephalography and Clinical Neurophysiology 76 (258-267) (1990).
8. Lim, C., Renniea, C., Barry, R., Bahramali, H., Lazzaro, I., Manor, B., Gordon, E. Decomposing skin conductance into tonic and phasic components. International Journal of Psychophysiology 25 (1997) 97-109.
9. FLIR Systems 70 Castilian Dr., Goleta, Calif. 93117: (http://www.flir.com).
10. ADInstruments 2005 Executive Circle, Colorado Springs, Colo. 80906. (http://www.adistruments.com).

The disclosures of all patents, patent applications, and publications cited herein are hereby incorporated by reference, to the extent they provide exemplary, procedural or other details supplementary to those set forth herein.

What is claimed is:

1. A system for quantifying at least one sympathetic response on the face, the system comprising:
   a thermal imager adapted to measure signals from at least one facial region selected from the group consisting of supraorbital, periorbital, and maxillary regions;
   wherein the measured signal is at least one selected from the group consisting of blood flow in the facial/ophthalmic arteriovenous complex, blood flow in the supraorbital area, perspiration in the supraorbital area, and perspiration in the maxillary area; and
   at least one ground-truth probe synchronized with the thermal imager via an electronic circuit.

2. The system of claim 1 wherein the at least one ground-truth probe is selected from GSR sensors, thermistor sensors, piezo-respiratory belt transducers, and combinations thereof.

3. The system of claim 1 further comprising a computer in communication with the thermal imager.

4. The system of claim 3 wherein the computer is adapted to perform wavelet energy analysis on the measured signal.

5. A method for quantifying at least one sympathetic response on the face, the method comprising measuring signals from at least one facial region selected from the group consisting of supraorbital, periorbital, and maxillary regions:

wherein said sympathetic responses are quantified through measurement or at least one selected from the group consisting of blood flow in the facial/ophthalmic arteriovenous complex, blood flow in the supraorbital area, perspiration in the supraorbital area, and perspiration in the maxillary area; and obtaining of at least one corroborating probe signal selected from perspiratory signals extracted through GSR, thermal signals extracted through thermistor sensors, and breathing signals extracted through a piezo-respiratory belt transducer.

6. The method of claim 5 comprising obtaining at least one measurement via thermal imaging.

7. The method of claim 5 wherein at least one of the corroborating probe signals is synchronized with the measurement via thermal imaging.

8. The method of claim 5 wherein the at least one sympathetic response is quantified through wavelets analysis.

9. The method of claim 8 comprising a multi-resolution wavelets approach.

10. A method of extracting a breathing component from thermal imaging signal data obtained from the maxillary area of the face, the method comprising:

performing multi-resolution wavelets analysis to determine phasic and tonic components; and examining the lower scale (higher frequency) wavelet energy for extraneous modulation indicative of a breathing component.

* * * * *